(12) United States Patent
Ratner et al.

(10) Patent No.: US 10,577,456 B2
(45) Date of Patent: Mar. 3, 2020

(54) HALOGENATED CYCLIC DIESTERS, RELATED POLYMERS, AND METHODS FOR THEIR PREPARATION AND USE

(71) Applicants: Buddy D. Ratner, Seattle, WA (US); Razieh Khalifehzadeh, Seattke, WA (US); Esmaeel Naeemi, Seattle, WA (US); Chang-Uk Lee, Seattle, WA (US); Andrew J. Boydston, Seattle, WA (US)

(72) Inventors: Buddy D. Ratner, Seattle, WA (US); Razieh Khalifehzadeh, Seattke, WA (US); Esmaeel Naeemi, Seattle, WA (US); Chang-Uk Lee, Seattle, WA (US); Andrew J. Boydston, Seattle, WA (US)

( * ) Notice: Subject to any disclaimer, the term of this patent is extended or adjusted under 35 U.S.C. 154(b) by 0 days.

(21) Appl. No.: 15/678,581

(22) Filed: Aug. 16, 2017

(65) Prior Publication Data

US 2017/0342205 A1 Nov. 30, 2017

Related U.S. Application Data

(63) Continuation-in-part of application No. PCT/US2016/018529, filed on Feb. 18, 2016.

(60) Provisional application No. 62/259,514, filed on Nov. 24, 2015, provisional application No. 62/117,900, filed on Feb. 18, 2015.

(51) Int. Cl.
| | | |
|---|---|---|
| C08G 63/02 | (2006.01) | |
| C08G 63/08 | (2006.01) | |
| C07D 319/12 | (2006.01) | |
| C08G 63/682 | (2006.01) | |
| A61L 31/06 | (2006.01) | |
| A61L 31/10 | (2006.01) | |
| C08G 63/91 | (2006.01) | |
| C08J 3/28 | (2006.01) | |
| C09D 167/04 | (2006.01) | |

(52) U.S. Cl.
CPC .............. *C08G 63/08* (2013.01); *A61L 31/06* (2013.01); *A61L 31/10* (2013.01); *C07D 319/12* (2013.01); *C08G 63/6822* (2013.01); *C08G 63/912* (2013.01); *C08J 3/28* (2013.01); *C09D 167/04* (2013.01); *C08J 2377/02* (2013.01)

(58) Field of Classification Search
USPC ......................................................... 525/415
See application file for complete search history.

(56) References Cited

PUBLICATIONS

Egitto et al. "Plasma modification of polymer surfaces for adhesion improvement"; IBM J. Res. Develop. vol. 38 Issue: 4; 1994 pp. 423-438. (Year: 1994).*

* cited by examiner

*Primary Examiner* — Terressa Boykin
(74) *Attorney, Agent, or Firm* — Olympic Patent Works PLLC

(57) ABSTRACT

Halogenated cyclic diesters, halogenated polymers derived from the cyclic diesters, and methods for making the halogenated cyclic diesters and related halogenated polymers.

12 Claims, 13 Drawing Sheets

$^1$H NMR spectrum of trifluoromethyl-substituted lactic acid monomers in acetonitrile-$d_3$.

$^{13}$C NMR spectrum of trifluoromethyl-substituted lactic acid monomers in acetonitrile-$d_3$.

$^{19}$F NMR spectrum of trifluoromethyl-substituted lactic acid monomers in acetonitrile-$d_3$.

$^1$H NMR spectrum of the purified trifluoromethyl-substituted polylactide in CDCl$_3$.

$^{19}$F NMR spectrum of purified trifluoromethyl-substituted polylactide in CDCl$_3$.

HALOGENATED CYCLIC DIESTERS, RELATED POLYMERS, AND METHODS FOR THEIR PREPARATION AND USE

CROSS-REFERENCE TO RELATED APPLICATIONS

This application is a continuation-in-part of PCT/US16/18529, filed Feb. 18, 2016, which claims the benefit of U.S. Patent No. 62/259,514, filed Nov. 24, 2015, and U.S. Patent No. 62/117,900, filed Feb. 18, 2015, each expressly incorporated herein by reference in its entirety.

BACKGROUND OF THE INVENTION

Polymers derived from lactic acid and glycolic acid have been extensively used for various biomedical applications due to their biocompatibility and biodegradability. The ability to modify the physiochemical properties, such as degradability, hydrophobicity, and hydrophilicity, of these polymers is a key to expand the spectrum of their uses. Conventional approaches usually involve copolymerization and block copolymer preparations. In contrast, the use of lactic acid and glycolic acid derivatives as monomers for preparing polylactides and polyglycolides is less well known.

Despites advances in the preparation of polylactides and polyglycolides, a need exists for the simple and versatile preparation of polylactides and polyglycolides having improved properties. The present invention seeks to fulfill these needs and provide further related advantages.

SUMMARY OF THE INVENTION

The present invention provides halogenated cyclic diesters, halogenated polymers derived from the cyclic diesters, and methods for making the halogenated cyclic esters and related halogenated polymers. In certain embodiments, the present invention provides fluorinated cyclic diesters, fluorinated polymers derived from these cyclic diesters, and methods for making the fluorinated cyclic diesters and related fluorinated polymers.

In one embodiment, the invention provides a cyclic diester having formula (I)

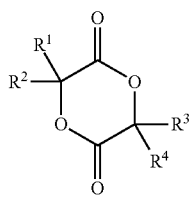

(I)

stereoisomers and racemates thereof,
wherein $R^1$, $R^2$, $R^3$, and $R^4$ are independently selected from hydrogen, C1-C24 alkyl, aryl, fluoro, chloro, and halocarbon, with the proviso that at least one of $R^1$, $R^2$, $R^3$, or $R^4$ is selected from fluoro, chloro, or halocarbon.

In another embodiment, the invention provides a cyclic diester having formula (I)

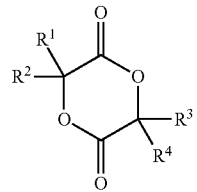

(I)

stereoisomers and racemates thereof,
wherein $R^1$, $R^2$, $R^3$, and $R^4$ are independently selected from hydrogen, C1-C24 alkyl, aryl, fluoro, and fluorocarbon (e.g., C1-C24 fluoroalkyl), with the proviso that at least one of $R^1$, $R^2$, $R^3$, or $R^4$ is selected from fluoro or fluorocarbon.

In certain embodiments, the fluorocarbon is a C1-C24 fluoroalkyl group. In other embodiments, the fluorocarbon is a C1-C12 fluoroalkyl group. In further embodiments, the fluorocarbon is a C1-C6 fluoroalkyl group.

In a further embodiment, the invention provides a cyclic diester having formula (II)

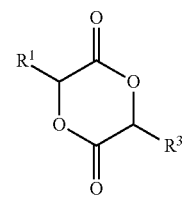

(II)

stereoisomers and racemates thereof,
wherein $R^1$ and $R^3$ are independently selected from C1-C24 alkyl and fluorocarbon (e.g., C1-C24 fluoroalkyl), with the proviso that at least on of $R^1$ or $R^3$ is fluorocarbon.

In another aspect, the invention provides polymers prepared from the cyclic diesters of the invention.

In one embodiment, the invention provides a halogenated polymer, comprising a repeating unit having formula (III)

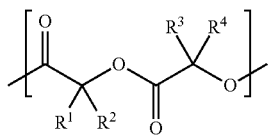

(III)

wherein
$R^1$, $R^2$, $R^3$, and $R^4$ are independently selected from hydrogen, C1-C24 alkyl, aryl, fluoro, chloro, and halocarbon, with the proviso that at least one of $R^1$, $R^2$, $R^3$, or $R^4$ is selected from fluoro, chloro, or halocarbon.

In another embodiment, the invention provides a fluorinated polymer, comprising a repeating unit having formula (III)

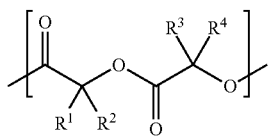

(III)

wherein
$R^1$, $R^2$, $R^3$, and $R^4$ are independently selected from hydrogen, C1-C24 alkyl, aryl, fluoro, and fluorocarbon (e.g., C1-C24 fluoroalkyl), with the proviso that at least one of $R^1$, $R^2$, $R^3$, or $R^4$ is selected from fluoro or fluorocarbon.

In one embodiment, the invention provides a halogenated polylactic acid, comprising a repeating unit having formula (IV)

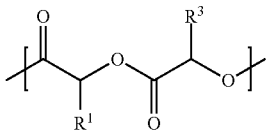

(IV)

wherein
$R^1$ and $R^3$ are independently selected from C1-C24 alkyl and halocarbon, with the proviso that at least one of $R^1$ or $R^3$ is halocarbon.

In another embodiment, the invention provides a fluorinated polylactic acid, comprising a repeating unit having formula (IV)

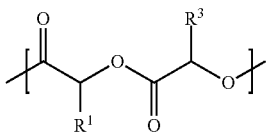

(IV)

wherein
$R^1$ and $R^3$ are independently selected from C1-C24 alkyl and fluorocarbon (e.g., C1-C24 fluoroalkyl), with the proviso that at least one of $R^1$ or $R^3$ is fluorocarbon.

In certain embodiments, the polymer of the invention further comprises one or more repeating units derived from comonomers suitable for polymerization with a halogenated cyclic diester.

In one embodiment, the invention provides a polymer having formula (V)

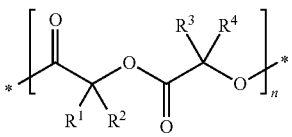

(V)

wherein
*represents the terminal groups of the polymer, and n is an integer from about 10 to about 1000.

In another embodiment, the invention provides a polylactic acid having formula (VI)

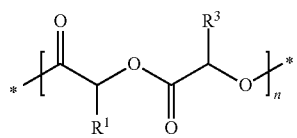

(VI)

wherein
*represents the terminal groups of the polymer, and
n is an integer from about 10 to about 1000.

In one embodiment, the invention provides a polymer having formula (VII)

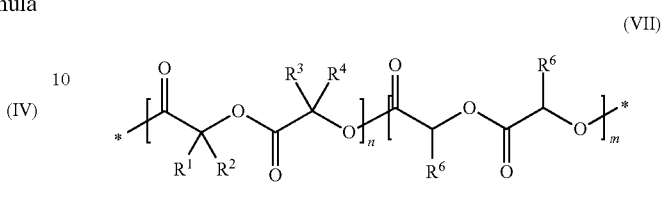

(VII)

wherein
$R^6$ is hydrogen or methyl,
n is an integer from about 10 to about 1000, and
m is an integer from about 10 to about 1000.

In another embodiment, the invention provides a polylactic acid having formula (VIII)

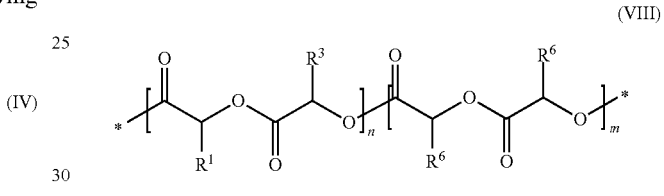

(VIII)

wherein
$R^6$ is hydrogen or methyl,
n is an integer from about 10 to about 1000, and
m is an integer from about 10 to about 1000.

In certain embodiments, the polymers of the invention are random copolymers. In other embodiments, the polymers of the invention are block copolymers.

In a further aspect of the invention, surfaces coated with a polymer of the invention are provided. In one embodiment, the invention provides a surface of a substrate, wherein at least a portion of the surface is coated with a polymer of the invention. Suitable substrates include drug delivery devices, devices having a degradation-inhibiting coating, devices having a hydrophobic surface with high contact angle, and devices that contact blood. In certain embodiments, the substrate is a medical device, such as a cardiovascular stent.

In another aspect, the invention provides methods for making halogenated polymers. In one embodiment, the method comprises:
subjecting a polymer with an ammonia plasma to provide a polymer functionalized with amino groups;
reacting the polymer functionalized with amino groups with a suitably reactive reagent comprising a halocarbon, wherein at least a portion of the amino groups react with the reagent to provide a polymer having at least of portion of the amino groups converted to amine groups covalently coupled to the halocarbon.

In another embodiment, the method comprises:
subjecting a polymer with an ammonia plasma to provide a polymer functionalized with amino groups;
reacting the polymer functionalized with amino groups with a suitably reactive reagent comprising a fluorocarbon (e.g., fluoroalkyl group), wherein at least a portion of the amino groups react with the reagent to provide a polymer having at least of portion of the amino groups converted to amine groups covalently coupled to the fluorocarbon.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Fluorinated polymers demonstrate excellent inertness in various biological environments and good blood compatibility, and have been used in various biomedical applications, such as prosthetics and drug delivery.

In one aspect, the present invention provides halogenated polymers and methods for their preparation. In the halogenated polymers of the invention, the structure of polymer backbone remains unchanged and this in turn results in retention of their hydrolysis characteristics. However, due to the introduction of halogens (i.e., fluorine or chlorine) into these polymers the halogenated (e.g., fluorinated and or chlorinated) polymers of the invention hydrolyze at a divers rate due to their increased hydrophobicity associated with the replacement of hydrogen in the parent polymers with a halogen (e.g., fluorine or chlorine), thereby expanding their performance in biological environments.

As used herein, the term "halogenated" or "halogen" refers to a cyclic diester or polymer that includes one or more chlorine and/or fluorine atoms.

The present invention provides halogenated cyclic diester, halogenated polymers derived from the cyclic diesters, and methods for making the halogenated cyclic esters and related halogenated polymers. In certain embodiments, the present invention provides fluorinated cyclic diesters, fluorinated polymers derived from the cyclic diesters, and methods for making the fluorinated cyclic diesters and related fluorinated polymers.

Cyclic Diesters

Figure 1:
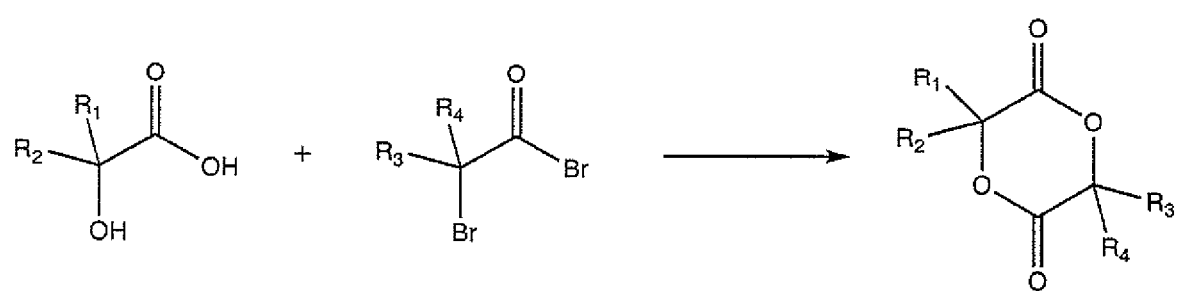
FIG. 1 is a schematic illustration of a representative preparation of cyclic diesters of the invention from alpha-hydroxy acids and reactive alpha-bromo alkanoyl bromide compounds.

In one aspect, the invention provides halogenated cyclic diesters (i.e., cyclic diesters that include one or more halogen substituents also referred to herein as halogen-containing cyclic diesters). The cyclic diesters of the invention can be prepared from alpha-hydroxy acids. See FIGS. 1-5 and 7. The cyclic diesters of the invention can be polymerized to provide polyesters that include fluorine and/or chlorine substituents. See FIGS. 6 and 7. The cyclic diesters of the invention are 6-membered ring compounds. In certain embodiments, the cyclic diester is a lactide or a lactide derivative. In other embodiments, the cyclic diester is a glycolide or a glycolide derivative. The cyclic diesters of the invention have the general structure shown in FIG. 1 where $R^1$-$R^4$ are as described below. FIG. 1 is a schematic illustration of a representative preparation of cyclic diesters of the invention from alpha-hydroxy acids and reactive alpha-bromo alkanoyl bromide compounds.

In one embodiment, the cyclic diester of the invention has formula (I)

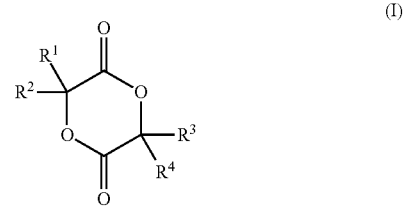

(I)

stereoisomers and racemates thereof, wherein $R^1$, $R^2$, $R^3$, and $R^4$ are independently selected from hydrogen, C1-C24 alkyl, aryl, fluoro, chloro, and halocarbon, with the proviso that at least one of $R^1$, $R^2$, $R^3$, or $R^4$ is selected from fluoro, chloro, or halocarbon.

As used herein, the term "halocarbon" refers to a substituent group that includes one or more carbons (e.g., C1-C24, C1-C12, or C1-C6) and one or more chlorine or fluorine atoms. The terms "halocarbon" and "halocarbon group" are used interchangeably. Suitable halocarbon groups include one or more chlorine atoms (chloro substituents), one or more fluorine atoms (fluoro substituents), or one or more chlorine atoms and one or more fluorine atoms (chloro and fluoro substituents). Representative halocarbon groups include —$CH_2Cl$, —$CH_2F$, and —$CH(Cl)F$ groups, among others.

In another embodiment, the cyclic diester of the invention has formula (I)

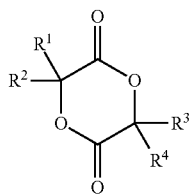

(I)

stereoisomers and racemates thereof, wherein $R^1$, $R^2$, $R^3$, and $R^4$ are independently selected from hydrogen, C1-C24 alkyl, aryl, fluoro, and fluorocarbon (e.g., C1-C24 fluoroalkyl), with the proviso that at least one of $R^1$, $R^2$, $R^3$, or $R^4$ is selected from fluoro or fluorocarbon.

As used herein, the term "fluoroocarbon" refers to a substituent group that includes one or more carbons (e.g., C1-C24, C1-C12, or C1-C6) and one or more fluorine atoms. The terms "fluorocarbon" and "fluorocarbon group" are used interchangeably. Suitable fluorocarbon groups include one or more fluorine atoms (fluoro substituents). Representative fluoroocarbon groups include —$CH_2F$, —$CHF_2$, and —$CF_3$ groups, among others. In certain embodiments, the fluorocarbon group is a C1-C24 fluoroalkyl group. In certain embodiments, C1-C24 alkyl is C1-C12 alkyl. In certain embodiments, C1-C24 alkyl is C1-C6 alkyl. Representative alkyl groups include straight chain (e.g., n-propyl), branched (e.g., isopropyl), and cyclo (e.g., C3-C7 cycloalkyl, such as cyclopentyl) groups. In certain embodiments, C1-C24 (or C1-C12 or C1-C6) alkyl is selected from methyl, ethyl, n-propyl, i-propyl, and n-butyl. In certain embodiments, C1-C24 (or C1-C12 or C1-C6) alkyl is methyl.

The alkyl and aryl groups of the cyclic diester may be substituted or unsubstituted. As used herein, the term "substituted C1-C24 alkyl" refers to a C1-C24 alkyl group in which one or more hydrogen atoms is replaced with a non-hydrogen atom. The term "substituted aryl" refers to an aryl group (e.g., phenyl group) in which one or more hydrogen atoms is replaced with a non-hydrogen atom. Representative non-hydrogen atoms include heteroatoms such oxygen, nitrogen, sulfur, and silicon atoms, as well as substituents that include these atoms (e.g., hydroxy, alkoxyl, amino, alkylamino, thiol, thioether).

In certain embodiments, the cyclic diesters of the invention include either a fluorine substituent or a fluoroalkyl substituent. As used herein the term "fluoroalkyl" or "fluoroalkyl group" refers to an alkyl group (i.e., a saturated hydrocarbon group) in which one or more hydrogen atoms is replaced with a fluorine atom (F). As used herein, the terms "fluoro" and "fluorine" are used interchangeably and refer to the substituent F. Representative fluoroalkyl groups include —$CF_3$, —$CH_2F$, —$CHF_2$, —$CF_2CF_3$, —$CH_2CF_3$, —$CF_2CH_3$, —$CH_2CHF_2$, —$CH_2CH_2F$, among others.

In certain embodiments, C1-C24 fluoroalkyl is C1-C12 fluoroalkyl. In certain embodiments, C1-C24 fluoroalkyl is C1-C6 fluoroalkyl.

Representative fluoroalkyl groups include straight chain (e.g., n-propyl), branched (e.g., isopropyl), and cyclo (e.g., C3-C7 cycloalkyl, such as cyclopentyl) groups. In certain embodiments, C1-C24 (or C1-C12 or C1-C6) fluoroalkyl is selected from methyl, ethyl, n-propyl, i-propyl, and n-butyl in which one or more hydrogen atoms is replaced with a fluorine atom. In certain embodiments, the fluoroalkyl is perfluoroalkyl (e.g., trifluoromethyl, pentafluoroethyl, n-perfluoropropyl, n-perfluorobutyl, and n-perfluoropentyl).

In certain embodiments, C1-C24 (or C1-C12 or C1-C6) alkyl is methyl (i.e., trifluoromethyl, difluoromethyl, and fluoromethyl).

In certain embodiments, the fluoroalkyl group(s) of the cyclic diester has a ratio of F:C from about 0.4 to about 3.0. In certain embodiments, the fluoroalkyl group(s) of the cyclic diester has a ratio of F:C of about 0.5. In other embodiments, the fluoroalkyl group(s) of the cyclic diester has a ratio of F:C of about 1.0. In further embodiments, the fluoroalkyl group(s) of the cyclic diester has a ratio of F:C of about 2.0.

In one embodiment of formula (I), $R^1$ and $R^3$ are hydrogen and $R^2$ and $R^4$ are trifluoromethyl.

In one embodiment of formula (I), $R^1$ and $R^3$ are hydrogen, $R^2$ is methyl, and $R^4$ is trifluoromethyl.

In one embodiment of formula (I), $R^1$ and $R^2$ are hydrogen and $R^3$ and $R^4$ are trifluoromethyl.

In one embodiment of formula (I), $R^1$, $R^2$, and $R^3$ are hydrogen and $R^4$ is trifluoromethyl.

In one embodiment of formula (I), $R^1$, $R^2$, $R^3$, and $R^4$ are trifluoromethyl.

In one embodiment of formula (I), $R^1$ and $R^2$ are hydrogen and $R^3$ and $R^4$ are fluoro.

In one embodiment of formula (I), $R^1$ is hydrogen, $R^2$ is methyl, and $R^3$ and $R^4$ are fluoro.

In one embodiment of formula (I), $R^1$, $R^2$, $R^3$, and $R^4$ are fluoro.

In another embodiment, the cyclic diester of formula (I) is a lactide having formula (II)

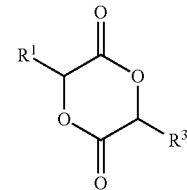

(II)

stereoisomers and racemates thereof, wherein $R^1$ and $R^3$ are independently selected from C1-C24 alkyl and fluorocarbon (e.g., C1-C24 fluoroalkyl), with the proviso that $R^1$ and $R^3$ at least one of $R^1$ and $R^3$ is fluorocarbon (e.g., C1-C24 fluoroalkyl). In this embodiment, $R^1$ and $R^3$ are as described above for formula (I).

In one embodiment of the lactide of formula (II), $R^1$ is methyl and $R^3$ is trifluoromethyl.

In one embodiment of the lactide of formula (II), $R^1$ is hydrogen and $R^3$ is trifluoromethyl.

In one embodiment of the lactide of formula (II), $R^1$ and $R^3$ are trifluoromethyl.

Figure 2:
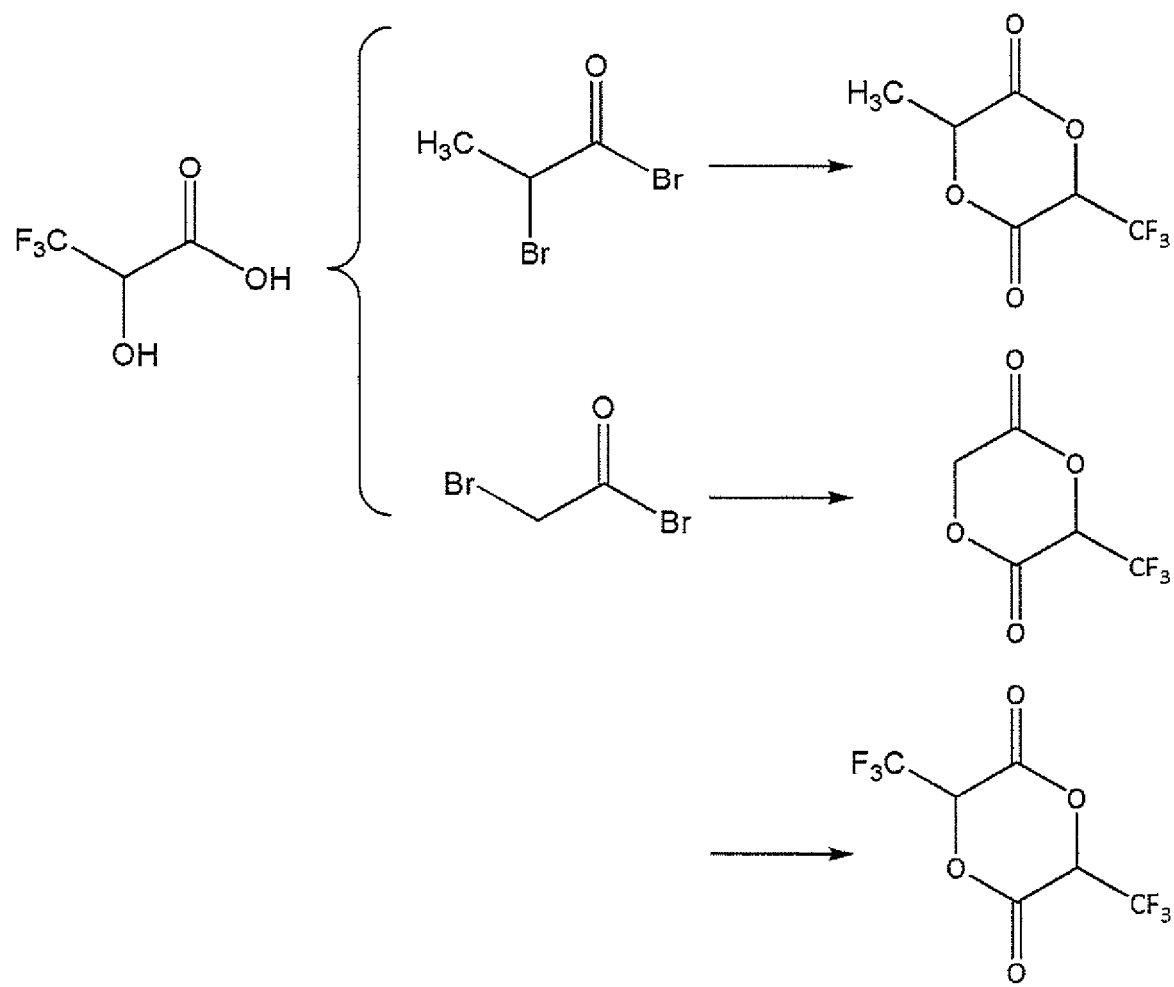
FIG. 2 is a schematic illustration of a representative preparation of cyclic diesters of the invention starting from the alpha-hydroxy acid: $CF_3CH(OH)$—$C(=O)OH$.
Figure 3:
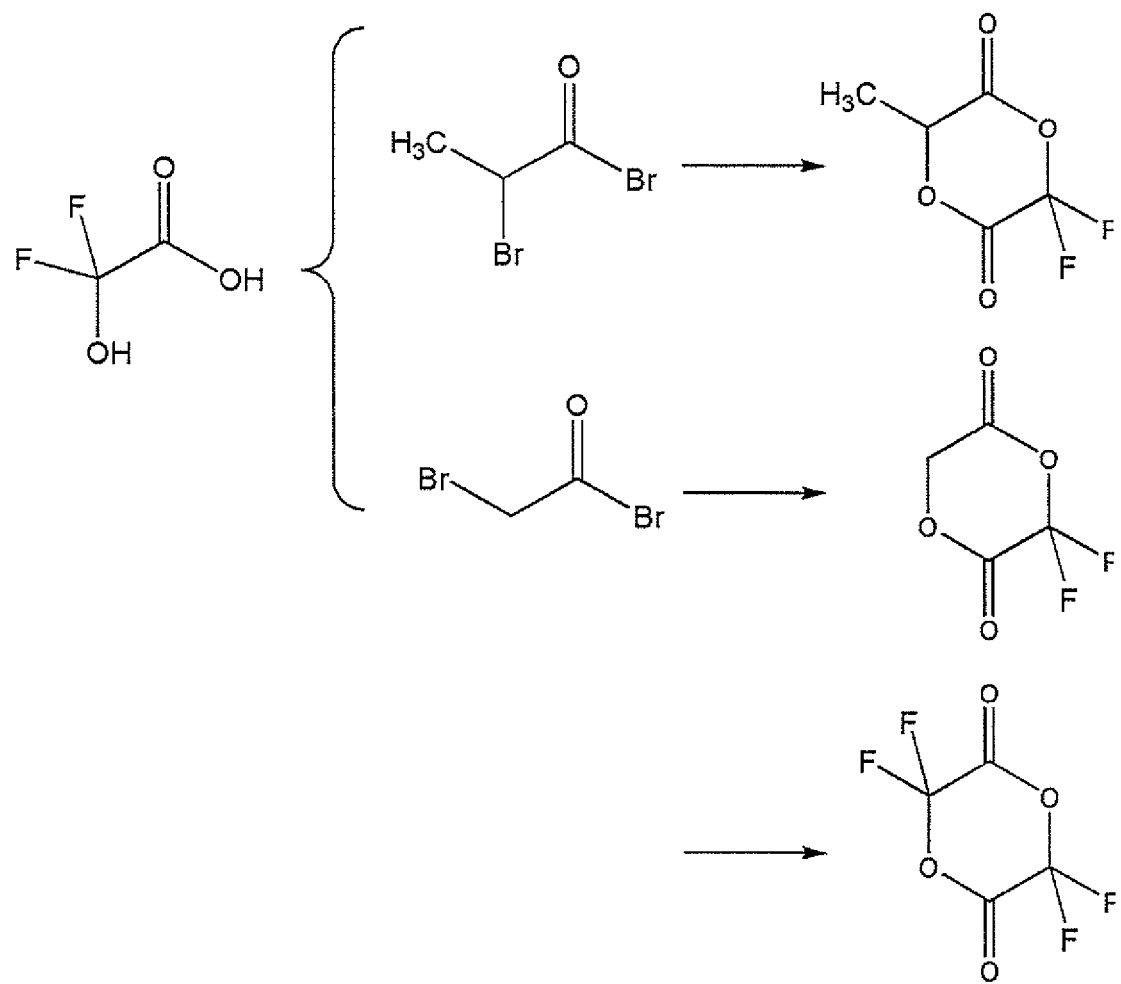
FIG. 3 is a schematic illustration of a representative preparation of cyclic diesters of the invention starting from the alpha-hydroxy acid: $CF_2(OH)$—$C(=O)OH$.
Figure 4:
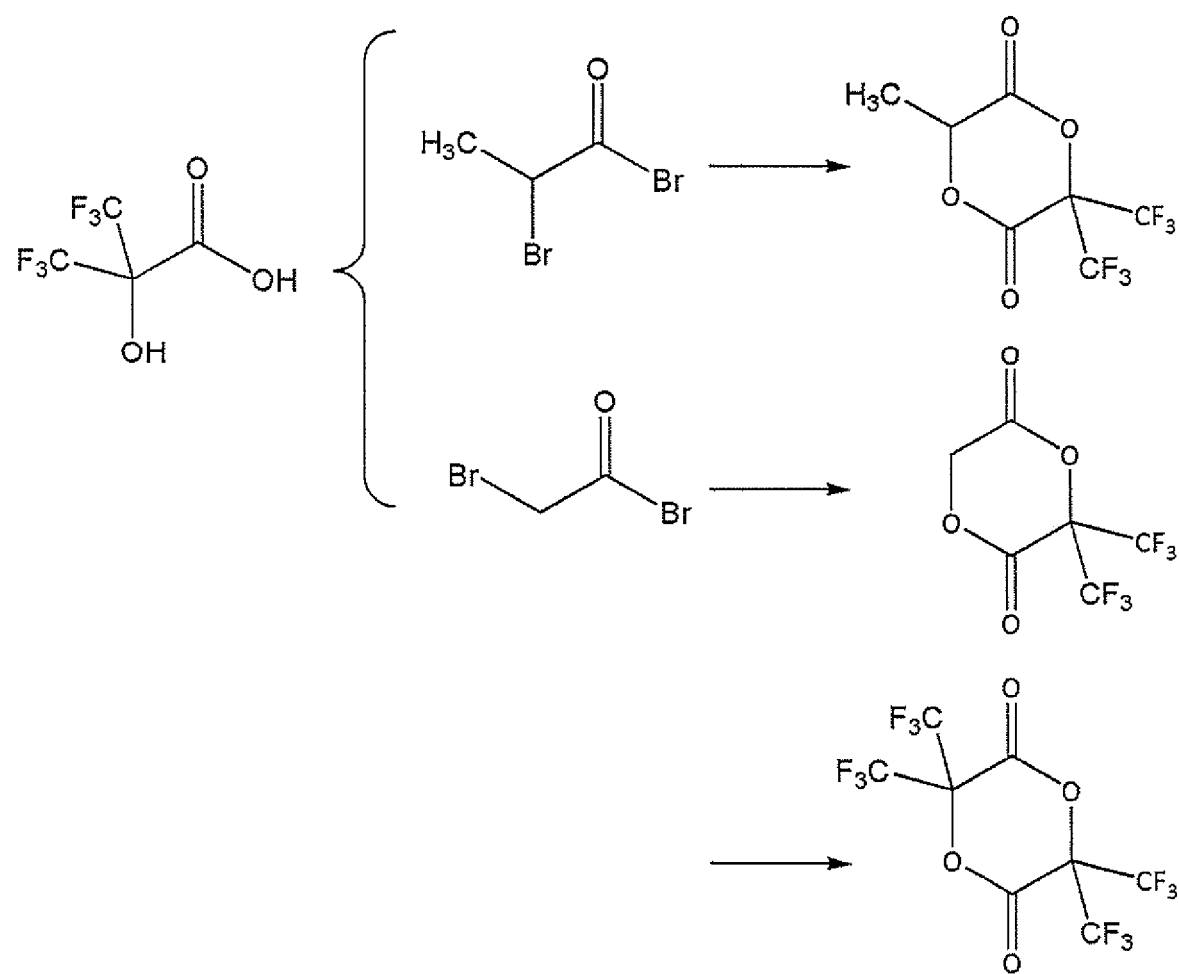
FIG. 4 is a schematic illustration of a representative preparation of cyclic diesters of the invention starting from the alpha-hydroxy acid: $(CF_3)_2C(OH)$—$C(=O)OH$.
Figure 5:
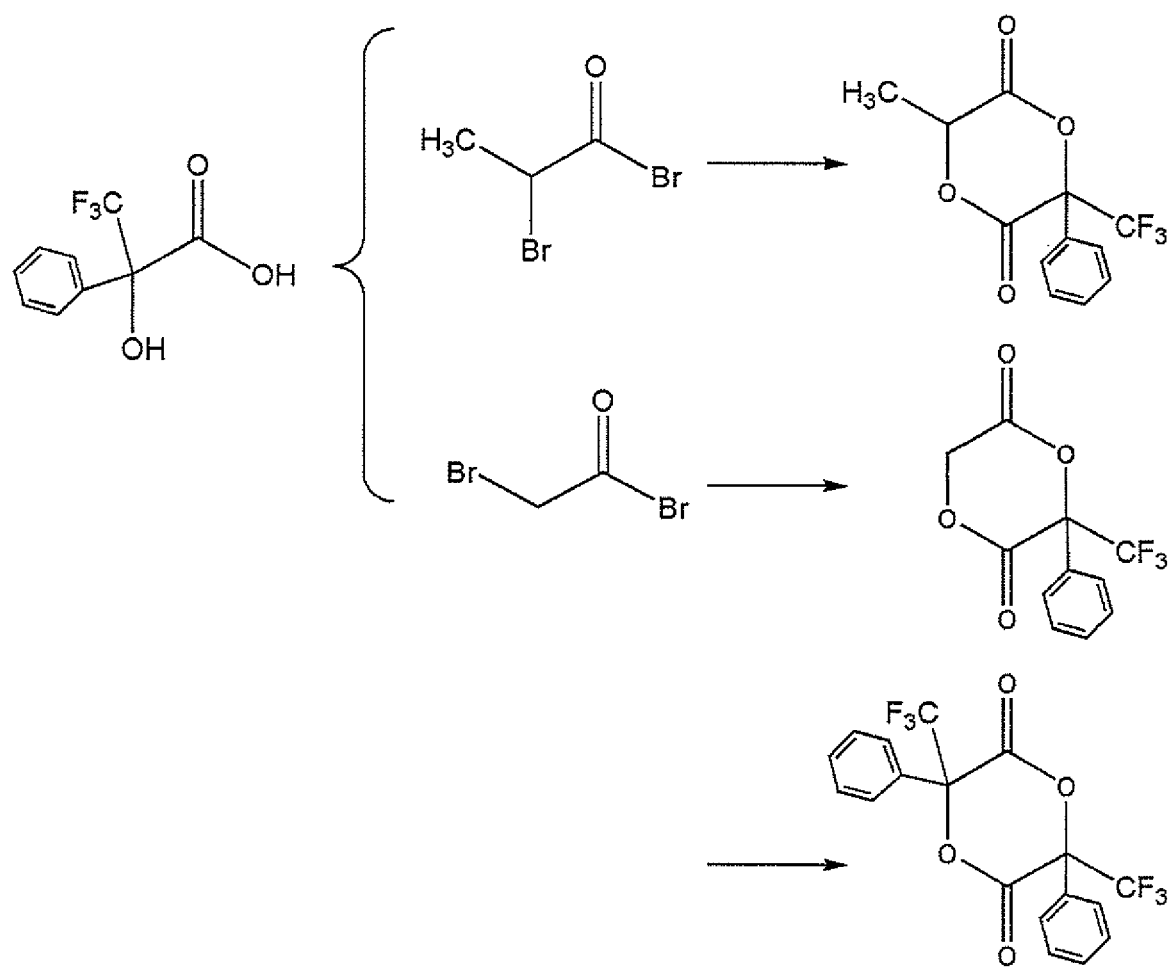
FIG. 5 is a schematic illustration of a representative preparation of cyclic diesters of the invention starting from the alpha-hydroxy acid: $CF_3C(Ph)(OH)$—$C(=O)OH$.

Representative cyclic diesters of the invention have the structures shown in FIGS. 2-5. FIG. 2 is an illustration of the preparation a representative cyclic diester starting from $CF_3CH(OH)$—$C(=O)OH$. FIG. 3 is an illustration of the preparation a representative cyclic diester starting from $CF_2(OH)$—$C(=O)OH$. FIG. 4 is an illustration of the preparation a representative cyclic diester starting from $(CF_3)_2C(OH)$—$C(=O)OH$. FIG. 5 is an illustration of the preparation a representative cyclic diester starting from $CF_3C(Ph)(OH)$—$C(=O)OH$.

Polymers

In another aspect, the invention provides halogenated polymers. As used herein the terms "halogenated polymer"

refers to a polymer that includes one or more chlorine and/or one or more fluorine atoms, and particularly to a polymer that includes repeating units derived from monomers that include one or more halogen atoms (e.g., fluorine and/or chlorine atoms) or halogen-containing substituents (i.e., halocarbon groups, such as chlorocarbon, fluorocarbon, or chloro/fluorocarbon groups). In certain embodiments, the polymers of the invention are prepared from the halogenated cyclic diesters of the invention. In certain embodiments, the halogenated polymers are prepared by ring opening polymerization. In other embodiments, the halogenated polymers are prepared by condensation polymerization.

In one embodiment, the invention provides fluorinated polymers. As used herein the terms "fluorinated polymer" refers to a polymer that includes fluorine atoms, and particularly to a polymer that includes repeating units derived from monomers that include one or more fluorine atoms or fluorine-containing substituents (e.g., fluorocarbon groups, such as fluoroalkyl groups). In one embodiment, the fluorinated polymers of the invention are prepared from the fluorinated cyclic diesters of the invention. In certain embodiments, the fluorinated polymers are prepared by ring opening polymerization. In other embodiments, the fluorinated polymers are prepared by condensation polymerization.

Figure 6:
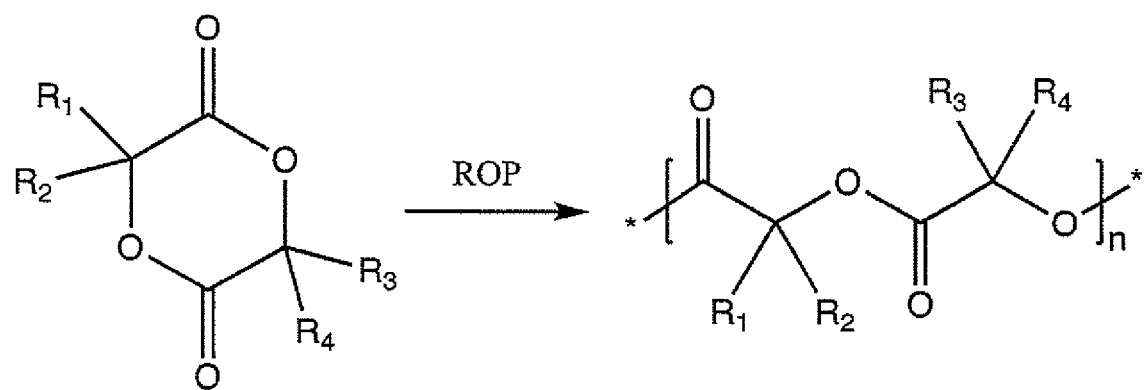
FIG. 6 is a schematic illustration of a representative preparation of fluorinated polymers of the invention from cyclic diesters.
Figure 7:
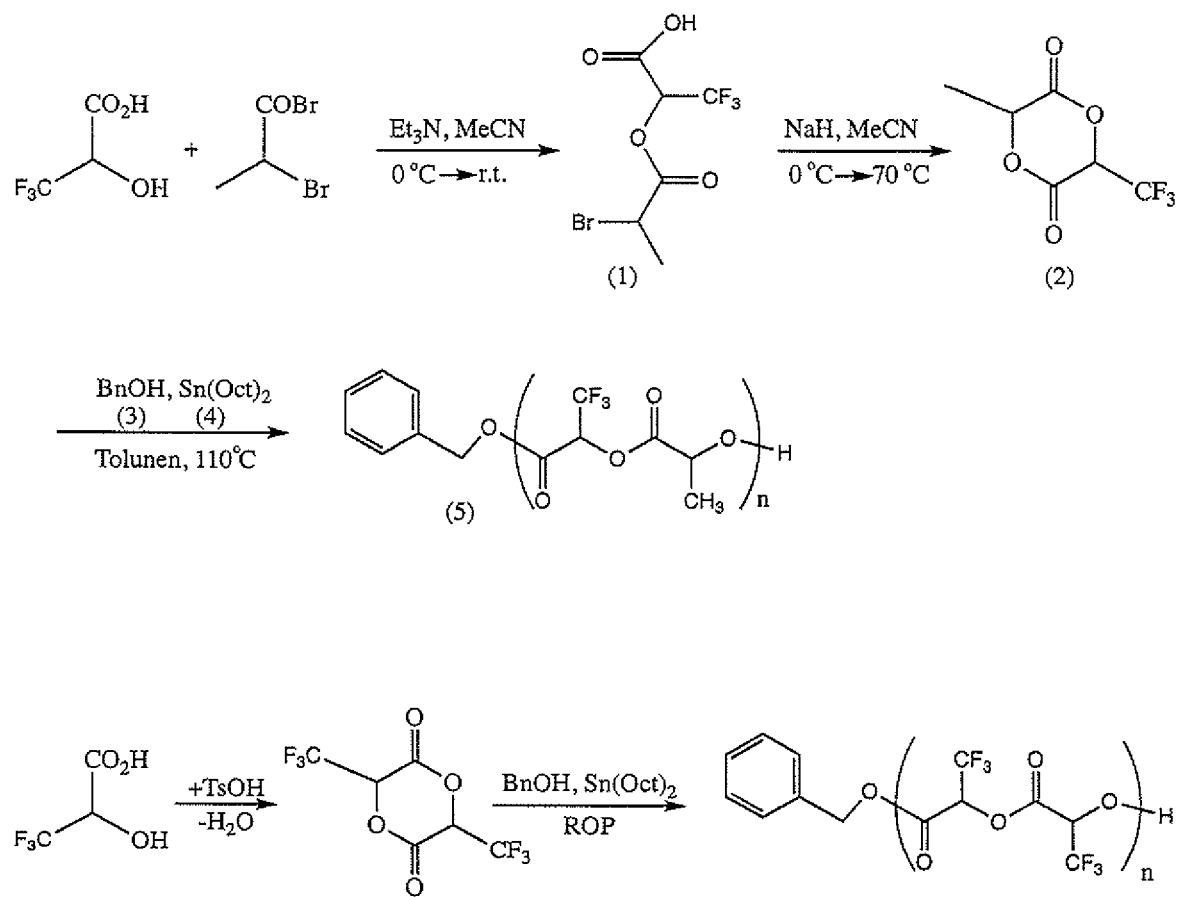
FIG. 7 is a schematic illustration of representative preparations of fluorinated polymers of the invention from cyclic diesters prepared from a representative alpha-hydroxy acid: $CF_3CH(OH)$—$C(=O)OH$.
Figure 8:
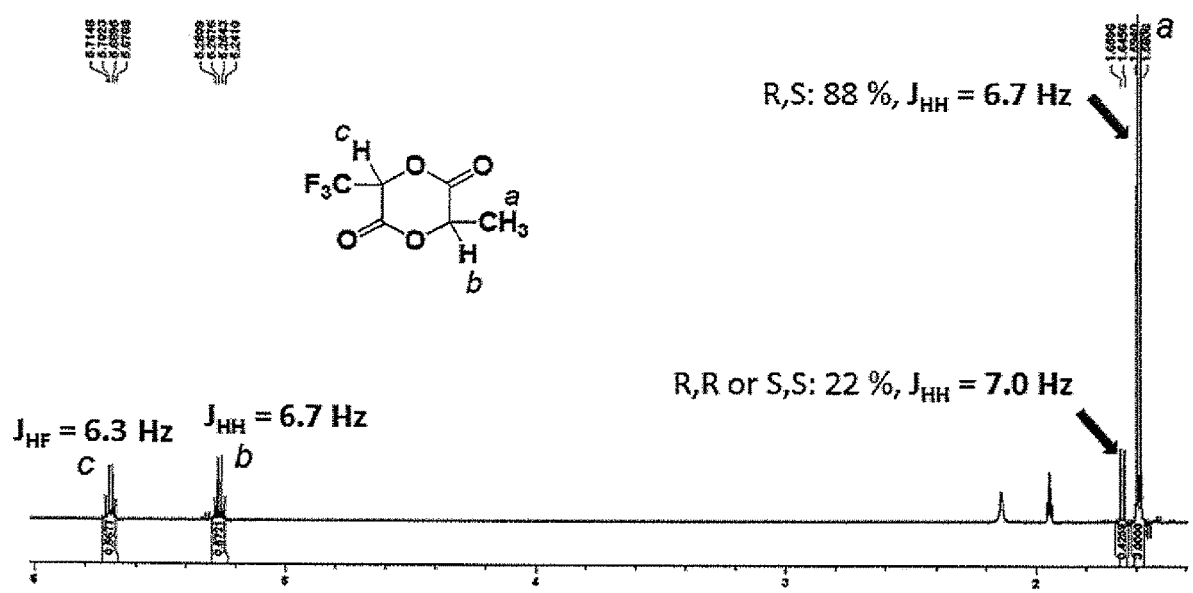
FIG. 8 is a $^1H$ NMR spectrum of trifluoromethyl-substituted lactic acid monomers in acetonitrile-$d_3$.

FIG. 6 is a schematic illustration of a representative preparation of fluorinated polymers of the invention from cyclic diesters. FIG. 7 is a schematic illustration of representative preparations of fluorinated polymers of the invention from cyclic diesters prepared from a representative alpha-hydroxy carboxylic acid: $CF_3CH(OH)—C(=O)OH$.

In certain embodiments, the halogenated polymer includes a repeating unit having formula (III)

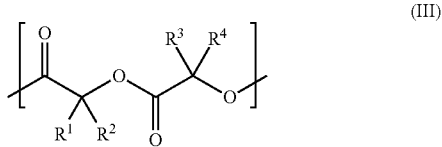

(III)

wherein $R^1$, $R^2$, $R^3$, and $R^4$ are independently selected from hydrogen, C1-C24 alkyl, aryl, fluoro, chloro, and halocarbon, with the proviso that at least one of $R^1$, $R^2$, $R^3$, or $R^4$ is selected from fluoro, chloro, or halocarbon.

In other embodiments, the fluorinated polymer includes a repeating unit having formula (III)

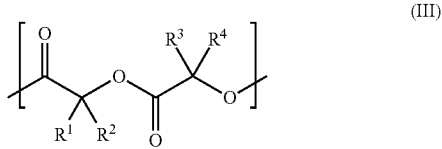

(III)

wherein $R^1$, $R^2$, $R^3$, and $R^4$ are independently selected from hydrogen, C1-C24 alkyl, aryl, fluoro, chloro, and halocarbon, with the proviso that at least one of $R^1$, $R^2$, $R^3$, or $R^4$ is selected from fluoro or fluorocarbon.

In certain embodiments, the halogenated polymer is a polylactic acid that includes a repeating unit having formula (IV)

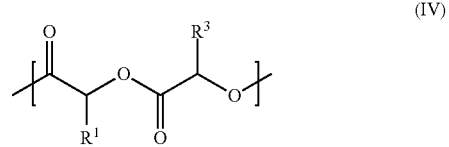

(IV)

wherein
$R^1$ and $R^3$ are independently selected from C1-C24 alkyl and halocarbon, with the proviso that at least one of $R^1$ or $R^3$ is halocarbon.

In other embodiments, the fluorinated polymer is a fluorinated polylactic acid that includes a repeating unit having formula (IV)

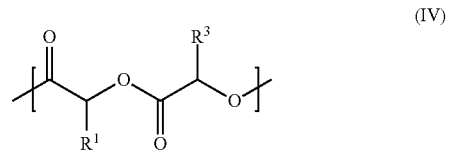

(IV)

wherein $R^1$ and $R^3$ are independently selected from C1-C24 alkyl and fluorocarbon (e.g., C1-C24 fluoroalkyl), with the proviso that at least one of $R^1$ and $R^3$ is fluorocarbon. $R^1$ and $R^3$ are as described above for the cyclic diesters.

In certain embodiments, the invention includes the polymers of formulae (III) and (IV) that further include one or more repeating units derived from comonomers suitable for polymerization with a halogenated (e.g., fluorinated) cyclic diester (e.g., ring opening polymerization or condensation polymerization). Suitable comonomers include cyclic diesters, such as lactides and lactide derivatives (e.g., non-halogenated lactides and non-halogenated lactide derivatives) and glycolides and glycolide derivatives (e.g., non-halogenated glycolides and non-halogenated glycolide derivatives), and other suitable polymerizable esters.

In certain embodiments, the halogenated (e.g., fluorinated) polymer has formula (V)

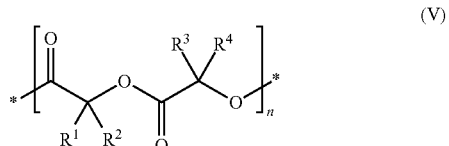

(V)

wherein *represents the terminal groups of the polymer, n is an integer from about 10 to about 1000, and $R^1$, $R^2$, $R^3$, and $R^4$ are as described above for the cyclic diesters.

The terminal groups of the polymer depend on the nature of the polymerization reaction used to form the polymer. For ring opening polymerizations, the terminal groups are derived from the initiator used in the polymerization. Suitable initiators useful in polymerizing cyclic diesters are known and include water and alcohols. When the initiator is water, one terminal group is —OH and the other is —H. When the initiator is an alcohol (ROH), one terminal group is —OR and the other is —H. Representative alcohols useful as initiators include methanol, 2-propanol, 2-methyl-2-propanol, 1-butanol, 4-phenyl-2-butanol, 1-hexanol, 1-decanol, 1-dodecanol, 1-tetradecanol, 1-hexadecanol, 1-octadecanol, 1-eicosanol, 1-docosanol, 1-pyrene butanol, and benzyl alcohol. In certain embodiments, the R group of the alcohol includes a functional group that allows for further functionalization of the product polymer.

In certain embodiments, the halogenated (e.g., fluorinated) polymer has formula (VI)

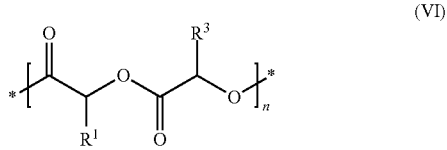

(VI)

wherein *represents the terminal groups of the polymer as defined above, n is an integer from about 10 to about 1000, and $R^1$ and $R^3$ are as described above for the cyclic diesters.

As noted above, in certain embodiments, n is an integer from about 10 to about 1000. In other embodiments, n is an integer from about 100 to about 10,000. In further embodiments, n is an integer from about 50 to about 500. In other embodiments, n is an integer from about 50 to about 2000.

In certain embodiments, the halogenated (e.g., fluorinated) polymer has formula (VII)

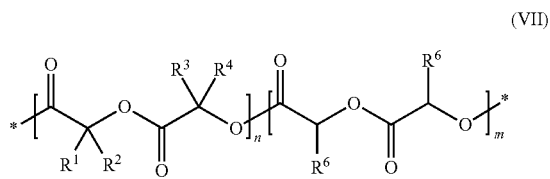

(VII)

wherein $R^1$ is hydrogen or methyl, n is an integer from about 10 to about 1000, m is an integer from about 10 to about 1000, and $R^1$, $R^2$, $R^3$, and $R^4$ are as described above for the cyclic diesters.

For the polymers of the invention, the ratio of n:m can vary depending on the desired degree of hydrophobicity and degradability (hydrolysis). In certain embodiments, n:m is about 1:100. In other embodiments, the ratio of nm is about 100:1. In further embodiments, the ratio of n:m is about 1:1. Other suitable n:m ratios include about 1:2, 1:3, 1:4, 1:5, 1:10, 1:20, 2:1, 3:1 4:1, 5:1, 10:1, and 20:1.

As used herein, the term "about" refers to +/−5% of the specified value.

In certain embodiments, the fluorinated polymer is a halogenated (e.g., fluorinated) polylactic acid having formula (VIII)

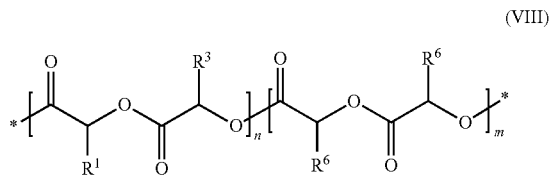

(VIII)

wherein $R^6$ is hydrogen or methyl, n is an integer from about 10 to about 1000, and m is an integer from about 10 to about 1000, the ratio of n:m is as described above for formula (VII), and $R^1$ and $R^3$ are as described above for the cyclic diesters.

As indicated above, certain of the polymers of the invention are homopolymers (i.e., include a single type of repeating unit). In certain embodiments, when the polymer includes two or more different types of repeating units, the polymer of the invention is a random copolymer. In other embodiments, when the polymer includes two or more different types of repeating units, the polymer of the invention is a block copolymer.

The polymers of the invention can be prepared from the cyclic diesters of the invention by polymerization methods. Suitable polymerization methods include polymerization methods known in the art for preparing polymers from cyclic diesters, and include ring opening polymerization methods and condensation polymerization methods. See, for example, U.S. Pat. Nos. 6,469,133 and 8,927,682, each expressly incorporated herein by reference in its entirety.

In a representative polymerization method, a cyclic diester and a suitable catalyst are combined in a solvent to provide a reaction mixture, the reaction mixture is heated to polymerize the cyclic ester to form the polymer in the reaction mixture (preferably the mixture is heated to a temperature between about 20° C. and 200° C.), and the polymer is isolated from the reaction mixture.

Suitable catalysts include those known in the art. Representative catalysts useful for preparing the fluorinated polymers of the invention from cyclic diesters include tin reagents such as $Sn(octanoate)_2$, $Sn(2-ethylhexanoate)_2$, $Sn(trifluoromethane\ sulfonate)_2$, $dibutylSn(2-ethylhexanoate)_2$, $Sn(phenyl)_4$, $Sn(bromide)_4$, $Sn(bromide)_2$, $Sn(oxide)$. Other suitable catalysts include 4-(dimethylamino)pyridine (DMAP). A representative procedure for the polymerization of a cyclic diester to provide a polymer of the invention is described in Example 2.

Polymer-Coated Substrates

In a further aspect, the invention provides substrates and surfaces coated with a polymer of the invention.

In one embodiment, the invention provides a surface of a substrate, wherein at least a portion of the surface is coated with a polymer of the invention (i.e., polymer of formulae (III)-(VIII). In certain embodiments, the substrate is useful as a drug delivery device, a device having a degradation-inhibiting coating, a device having hydrophobic surfaces with high contact angle, and a device that contacts blood. In certain embodiments, the substrate is a medical device, such as a cardiovascular stent.

Ammonia Plasma Process

In another aspect of the invention, a method for making a halogenated polymer is provided. In the method, halocarbon groups are introduced into the polymer.

In one embodiment, the method includes:
subjecting a polymer with an ammonia plasma to provide a polymer functionalized with amino groups;
reacting the polymer functionalized with amino groups with a suitably reactive reagent comprising a halocarbon, wherein at least a portion of the amino groups react with the reagent to provide a polymer having at least of portion of the amino groups converted to amine groups covalently coupled to the halocarbon.

In another embodiment, the method includes:
subjecting a polymer with an ammonia plasma to provide a polymer functionalized with amino (—$NH_2$) groups;
reacting the polymer functionalized with amino groups with a suitably reactive reagent comprising a fluorocarbon (e.g., fluoroalkyl) group, wherein at least a portion of the amino groups react with the reagent to provide a polymer having at least of portion of the amino groups converted to amine groups covalently coupled to the fluorocarbon groups.

Figure 13:
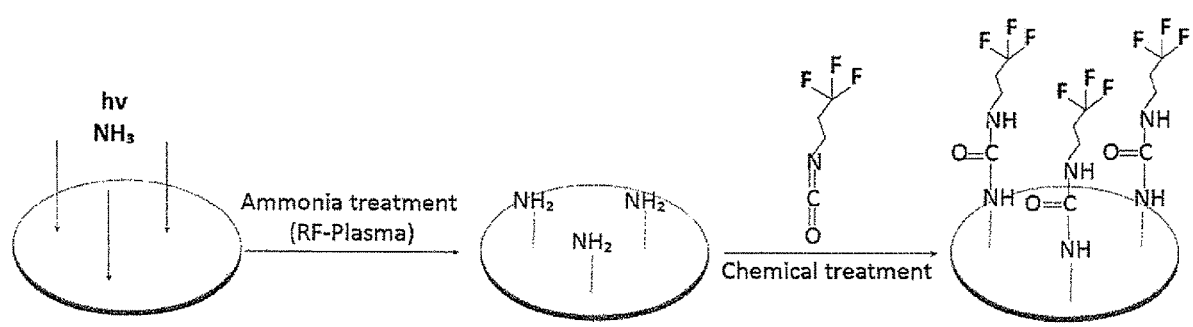
FIG. 13 is a schematic illustration of the preparation of fluorinated polymers of the invention prepared from reaction of suitably reactive fluoroalkyl reagents with amino-containing polymers prepared by treatment of suitable polymers with ammonia plasma.

An embodiment of the method is illustrated schematically in FIG. 13. Methods for imparting amino groups to a polylactic acid film by ammonia plasma treatment are described in J. Biomedical Materials Research B: Applied Biomaterials, February 2014, Vol. 102B, Issue 2, pages 345-355, expressly incorporated herein by reference in its entirety.

Suitable polymers useful in the method include polymers that can be modified by ammonia plasma to provide a polymer functionalized with amino groups. Polymers that are advantageously treated by the method of the invention include biocompatible, biodegradable polymers. Representative polymers include polylactic acids, polyglycolic acids, and poly(lactic-co-glycolic) acids.

Suitably reactive reagents comprising a halocarbon group have a reactive group capable of forming a covalent bond with the amino group imparted to the polymer by ammonia plasma. Representative reactive groups are selected from a carboxylic acid, carboxylic acid halide, carboxylic acid ester (NHS and fluorophenyl esters), isocyanate, isothiocyanate, acyl azide, aldehyde, epoxide, oxirane, carbonate, sulfonyl chloride, aryl halide, imidoester, glyoxal, carbodiimide, and anhydride. These reactive groups are covalently coupled to the amine groups by either alkylation or acylation.

Suitably reactive reagents comprising a fluorocarbon (e.g., fluoroalkyl) group have a reactive group capable of forming a covalent bond with the amino group imparted to the polymer by ammonia plasma. Representative reactive groups are selected from a carboxylic acid, carboxylic acid halide, carboxylic acid ester (NHS and fluorophenyl esters), isocyanate, isothiocyanate, acyl azide, aldehyde, epoxide, oxirane, carbonate, sulfonyl chloride, aryl halide, imidoester, glyoxal, carbodiimide, and anhydride. These reactive groups are covalently coupled to the amine groups by either alkylation or acylation.

In certain embodiments, the fluorocarbon is a fluoroalkyl group. In certain embodiments, the fluoroalkyl group is a C1-C24 fluoroalkyl group. In certain embodiments, the C1-C24 fluoroalkyl group is a C1-C12 fluoroalkyl group. In other embodiments, the C1-C24 fluoroalkyl group is a C1-C6 fluoroalkyl group. Representative fluoroalkyl groups include those described above for the cyclic diesters.

In certain embodiments of the method, the polymer subjected to ammonia plasma is a coating on at least a portion of a surface of a substrate. Suitable substrates include drug delivery devices, devices having a degradation-inhibiting coating, devices having a hydrophobic surface with high contact angle, and a device that contacts blood. In certain embodiments, the substrate is a medical device. In certain embodiments, the substrate is a cardiovascular stent.

In a further aspect, the invention provides a polymer prepared by the above ammonia plasma method. In one embodiment, the invention provides a surface of a substrate having at least a portion of the surface is coated with a polymer prepared by the above ammonia plasma method.

The following examples are provided for the purpose of illustrating, not limiting the invention.

EXAMPLES

Example 1

Preparation and Characterization of a Representative Cyclic Diester

In this example, preparations and characterization of representative cyclic diesters of the invention is described. The preparation is schematically illustrated in FIGS. 2 and 7.

Materials and Methods $^1$H, $^{13}$C NMR, and $^{19}$F NMR spectra were recorded on a Bruker AV 300, 500, and DRX 499 spectrometer, respectively. Chemical shifts are reported in delta (δ) units, expressed in parts per million (ppm) downfield from tetramethylsilane using the residual protio-solvent as an internal standard (CDCl$_3$, $^1$H: 7.26 ppm and $^{13}$C: 77.16 ppm, CD$_3$CN, $^1$H: 1.94 ppm and $^{13}$C: 118.36 ppm). For $^{19}$F NMR spectra, hexafluorobenzene (−164.9 ppm) was used as an internal standard in deuterated acetonitrile for monomer and deuterated chloroform for polymer.

Monomer Synthesis

FIG. 7 shows the synthetic rout for preparing trifluoromethyl-substituted lactic acid (2) monomer. Under nitrogen gas flow, trifluorolactic acid (6.2 g, 43 mmol) was added to a dry round bottom flask containing 70 ml dry acetonitrile and triethylamine (5.6 g, 7.8 mL, 56 mmol). The mixture was stirred and cooled in an ice bath. Then a solution of 2-bromopropionyl bromide (11.6 g, 5.7 mL, 54 mmol) in 10 mL of dry acetonitrile was added dropwise to the reaction mixture. After the addition was complete, the ice bath was removed and the mixture was stirred at room temperature for 3 h. The resulting white precipitate was filtered off through Celite, and the filtrate was concentrated under reduced pressure. The resulting product was then dissolved in ethyl acetate and filtered again to remove any remaining salts. The removal of the ethyl acetate by rotary evaporation gave product (1) as a brown oil, which was used without further purification for the next step.

For the synthesis of (2), sodium hydride (60%, 2.6 g, 64.5 mmol) was stirred in dry acetonitrile (800 mL) in an ice bath under nitrogen gas flow. Next, solution of product (1) in dry acetonitrile (100 mL) was added dropwise to the sodium hydride mixture for 30 mins. The ice bath was then removed, and the reaction mixture was stirred at room temperature for 1 h. Afterward, the resulting mixture was heated to 70° C., and stirred overnight under nitrogen gas atmosphere. Once the reaction was completed as shown by thin-layer chromatography (TLC), the resulting mixture was cooled to room temperature and white precipitate was filtered off through Celite and filtrate was concentrated. The product was then dissolved in dry ethyl acetate and filtered off through Celite to remove any residual salts. The filtrate was concentrated under reduced pressure, and purified by silica gel column chromatography using dry premium grade silica gel and a mixture of 30% dry ethyl acetate/hexanes as an eluent under nitrogen gas flow. The resulting product was further purified by recrystallization in dry DCM/hexanes to give a white solid as a mixture of R,S (88%, ⅞) and R,R/S,S (12%, ⅛) diastereomers which was analyzed by NMR (2.27 g, 27% yield). $^1$H NMR (500 MHz, CD$_3$CN) δ 5.71 (q, J=7.5 Hz, 1H×⅛), 5.69 (q, J=6.3 Hz, 1H×⅞), 5.31 (q, J=7.0 Hz, 1H×⅛), 5.26 (q, J=6.7 Hz, 1H×⅞), 1.65 (d, J=7.0 Hz, 3H×⅛), 1.58 (d, J=6.7 Hz, 3H×⅞). $^{13}$C NMR (126 MHz, CD$_3$CN) δ 165.8, 161.0, 121.4 (q, 1JCF=278 Hz, CF$_3$), 73.7, 73.0 (q, 2JCF=33 Hz, CF$_3$C—), 15.6. $^{19}$F NMR (471 MHz, CD$_3$CN, C$_6$F$_6$) δ −75.3.

Results

Figure 9:
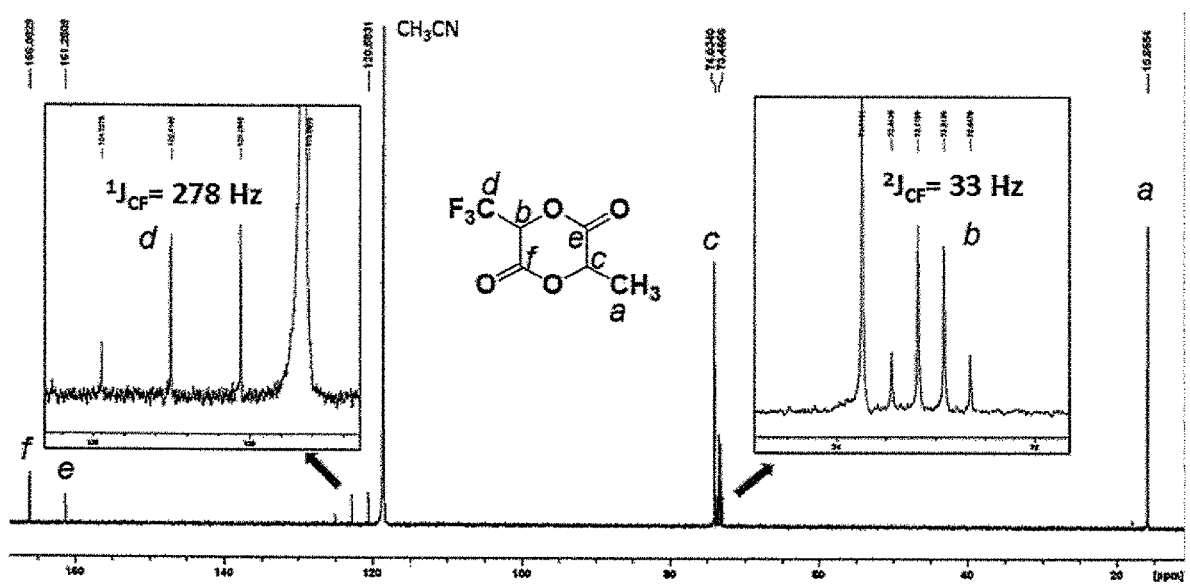
FIG. 9 is a $^{13}C$ NMR spectrum of trifluoromethyl-substituted lactic acid monomers in acetonitrile-$d_3$.
Figure 10:
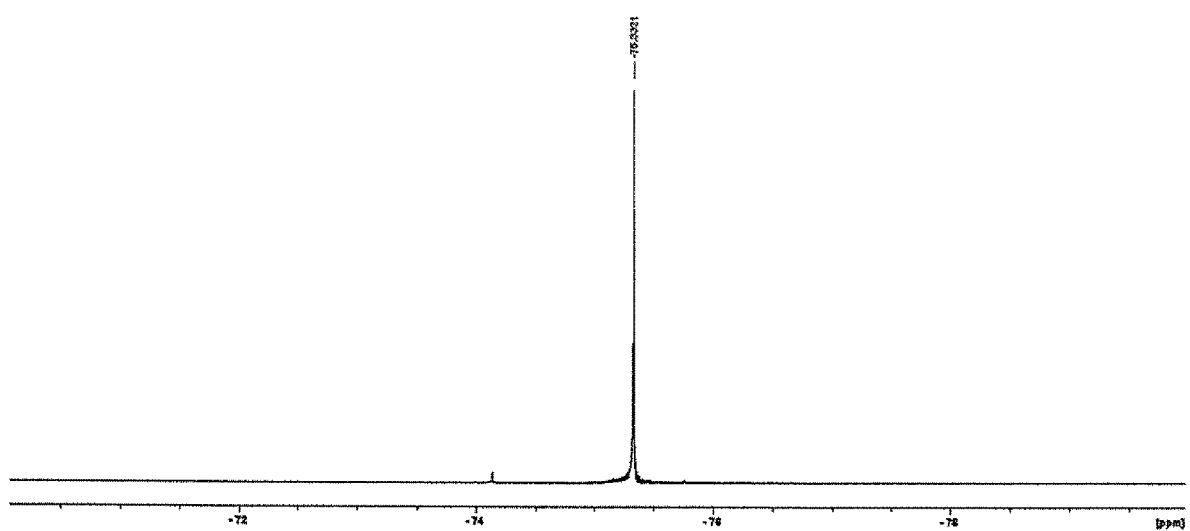
FIG. 10 is a $^{19}F$ NMR spectrum of trifluoromethyl-substituted lactic acid monomers in acetonitrile-$d_3$.
Figure 11:
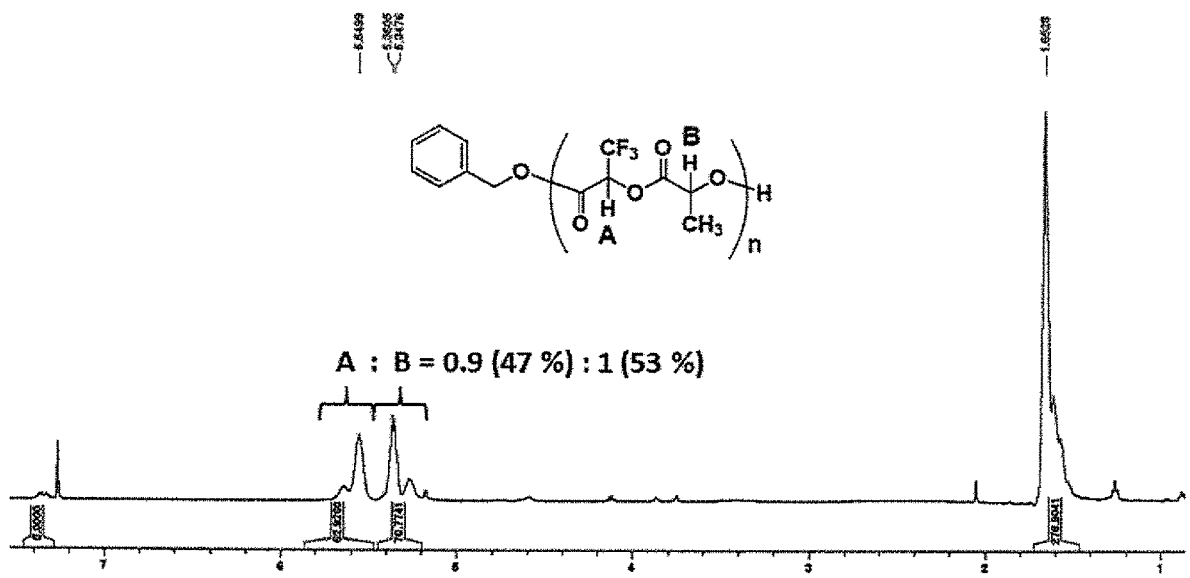
FIG. 11 is a $^1H$ NMR spectrum of the trifluoromethyl-substituted polylactide in $CDCl_3$.

The molecular structure of trifluoromethyl-substituted lactic acid (2) monomer was confirmed by $^1$H, $^{13}$C, and $^{19}$F NMR spectroscopy. In $^1$H NMR (FIG. 9), the doublet from the methyl protons of R,S isomers is shown with coupling constant of $J_{HH}$=6.7 Hz, and that from R,R or S,S isomers is shown with $J_{HH}$=7.0 Hz. The methine protons next to the trifluoromethyl groups of the R,S isomers are deshielded due to the electron withdrawing trifluoromethyl groups, downfielded, and shown at 5.7 ppm, compared to the methine protons next to the methyl groups at 5.25 ppm. In addition, coupling constant ($J_{HF}$=6.3 Hz) of the quartet from the methine protons next to the trifluoromethyl groups is distinct from that ($J_{HH}$=6.7 Hz) next to the methyl groups. The equal integration from these methine groups confirms the presence of the monomer (2). The structure of the monomer (2) is further verified by $^{13}$C NMR and $^{19}$F NMR spectroscopy (FIGS. 10 and 11). $^{13}$C NMR spectra (FIG. 10) shows the quartet (at 121.4 ppm, $^2J_{CF}$=278 Hz) from carbons of the trifluoromethyl groups due to carbon-fluorine couplings. In addition, it shows another quartet (at 73 ppm with $^1J_F$=33 Hz) from carbons next to the trifluoromethyl groups, which is distinct from the singlet (at 73.7 ppm) from carbons next to the methyl groups.

Example 2

Representative Method for Polymerizing a Cyclic Diester

The solution polymerization was conducted in toluene at 110° C. using benzyl alcohol as an initiator and tin(II) 2-ethylhexanoate (Sn(Oct)$_2$) as a catalyst. The initiator and catalyst were purified by distillation prior to polymerization, and their stock solutions in dry benzene (0.1 M) were prepared. In a dry box, monomer (2, 198 mg, 1 mmol) were placed into a vial with dry toluene (4 mL, 0.25 M). Then stock solutions of Sn(Oct)$_2$ (4, 100 µL, 0.01 mmol) and benzyl alcohol (3, 100 µL, 0.01 mmol) were added to the monomer solution. The vial was sealed with a Teflon cap and heated to 110° C. After 24 h, the mixture was cooled to room temperature and the product was dried under vacuum to remove solvent, catalyst and unreacted initiators. The crude polymer was dissolved in chloroform and filtered to selectively remove unreacted monomers. The chloroform was removed and the resulting solid product was stirred in methanol and dried under high vacuum to further remove any unreacted monomers. The resulting polymer was then dissolved in chloroform and precipitated in hexanes. The final product was obtained after removing hexanes and drying as a white powder (135 mg, 68% yield).

Results

Figure 12:
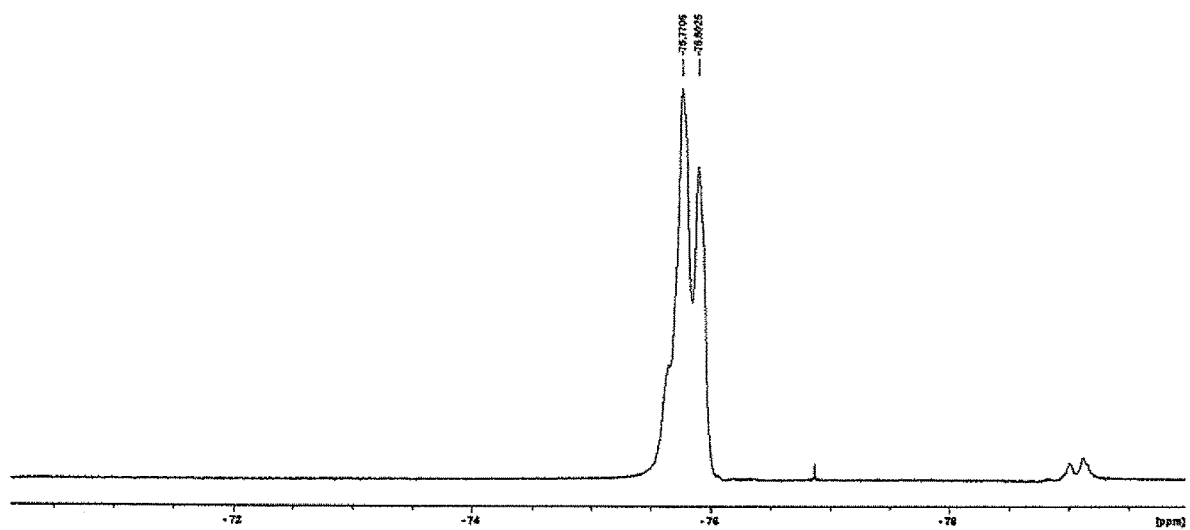
FIG. 12 is a $^{19}F$ NMR spectrum of trifluoromethyl-substituted polylactide in $CDCl_3$.

Polymerization was conducted by ring opening polymerization of the fluorine-substituted, cyclic diester monomers in solution using toluene as a solvent, benzyl alcohol as an initiator, and tin (11) 2-ethylhexanoate as a catalyst. The catalyst to initiator ratio was 1:1 for all polymerizations, and the monomer to initiator ratio was 100:1. The monomer was not very soluble in toluene at room temperature, but became soluble at 110° C. and reaction mixture remained homogeneous at 110° C. during polymerization. FIG. 11 shows the $^1$H NMR spectrum of the resulted trifluomethyl-substituted polylactide. The methine protons next to the trifluoromethyl groups are clearly shown from 5.47 to 5.7 ppm, and methine protons next to the methyl groups are from 5.2 to 5.45 ppm. The ratio of integration of the peaks from protons next to the trifluoromethyl groups to those next to the methyl groups is 0.9, indicating approximately equal portions of trifluoromethyl and methyl groups in the backbones of polymer. This NMR analysis suggests the structure of alternating trifluoromethyl and methyl groups. In addition, $^{19}$F NMR spectrum (FIG. 12) of the trifluomethyl-substituted polylactide shows broad peaks compared to the $^{19}$F NMR spectrum of monomer (FIG. 10), indicating the distribution of polymer chains with different molecular weights.

The invention claimed is:

1. A method for making trifluoromethyl-functionalized poly(lactic acid), the method comprising:
   preparing a brown oil containing trifluoromethyl-functionalized lactide monomer by adding, to trifluorolactic acid dissolved in acetonitrile, triethylamine followed by 2-bromopropionyl bromide; and
   adding the brown oil to a mixture of sodium hydride and acetonitrile.

2. The method of claim 1 wherein the trifluorolactic acid dissolved in acetonitrile is prepared by:
   under nitrogen gas flow, adding the trifluorolactic acid to a dry round bottom flask containing dry acetonitrile and triethylamine to prepare a mixture of trifluorolactic acid, triethylamine, and acetonitrile; and
   stirring and cooling the mixture of trifluorolactic acid, triethylamine, and acetonitrile in an ice bath.

3. The method of claim 2 wherein the 2-bromopropionyl bromide is added by:
   preparing a solution of 2-bromopropionyl bromide in acetonitrile; and
   dropwise adding the solution of 2-bromopropionyl bromide in acetonitrile solution to the trifluorolactic acid, triethylamine, and acetonitrile mixture to produce a first reaction mixture.

4. The method of claim 3 further comprising:
   stirring the first reaction mixture at room temperature for 3 hours;
   filtering a white precipitate from the first reaction mixture and concentrating the filtrate under reduced pressure to produce trifluoromethyl-functionalized-lactide-monomer product;
   dissolving the trifluoromethyl-functionalized-lactide-monomer product in ethyl acetate;
   filtering the trifluoromethyl-functionalized-lactide-monomer product in ethyl acetate to remove any remaining salts; and
   removing ethyl acetate by rotary evaporation to produce a brown oil.

5. The method of claim 1 wherein the mixture of sodium hydride and acetonitrile is prepared by stirring sodium hydride in dry acetonitrile in an ice bath under nitrogen gas flow.

6. The method of claim 5 further comprising:
   adding the brown oil to dry acetonitrile.

7. The method of claim 6 further comprising:
   dropwise adding the mixture of blown oil and acetonitrile to the mixture of sodium hydride and acetonitrile to produce a second reaction mixture.

8. The method of claim 7 further comprising: stirring the second reaction mixture at room temperature for 1 hour.

9. The method of claim 8 further comprising:
   heating and stirring the second reaction mixture under a nitrogen-gas atmosphere.

10. The method of claim 9 further comprising:
    cooling the second reaction mixture to room temperature;
    filtering a white precipitate from the second reaction mixture; and
    concentrating the filtrate was concentrated to produce the trifluoromethyl-functionalized-poly(lactic acid) product.

11. The method of claim 10 further comprising:
dissolving the trifluoromethyl-functionalized-poly(lactic acid) in dry ethyl acetate;
filtering the trifluoromethyl-functionalized-poly(lactic acid) in dry ethyl acetate to remove any residual salts;
concentrating the filtrate under reduced pressure; and
purifying the concentrate by silica gel column chromatography using dry premium grade silica gel and a mixture of 30% dry ethyl acetate/hexanes as an eluent under nitrogen gas flow.

12. The method of claim 11 further comprising:
further purifying the concentrate by recrystallization in dry methylenechloride hexane to produce a white solid.

* * * * *

UNITED STATES PATENT AND TRADEMARK OFFICE
CERTIFICATE OF CORRECTION

| | | |
|---|---|---|
| PATENT NO. | : 10,577,456 B2 | Page 1 of 1 |
| APPLICATION NO. | : 15/678581 | |
| DATED | : March 3, 2020 | |
| INVENTOR(S) | : Buddy D. Ratner et al. | |

It is certified that error appears in the above-identified patent and that said Letters Patent is hereby corrected as shown below:

On the Title Page

Item (71), delete the word "Seattke" and insert the word -- Seattle --.

Signed and Sealed this
Fifth Day of May, 2020

Andrei Iancu
*Director of the United States Patent and Trademark Office*